United States Patent
Siddiqui et al.

(10) Patent No.: US 6,322,752 B1
(45) Date of Patent: *Nov. 27, 2001

(54) METHOD AND APPARATUS FOR ASPIRATING AND DISPENSING LIQUIDS

(75) Inventors: Imran T. Siddiqui, Westchester, PA (US); Roberto del Valle, Coral Gables, FL (US); Santos Vargas, Miami Lakes, FL (US); Pedro P. Cabrera, Miami Lakes, FL (US)

(73) Assignee: Coulter International Corp., Miami, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/392,161

(22) Filed: Sep. 8, 1999

(51) Int. Cl.[7] .............................. B01L 3/02; B01L 11/00; G05B 1/00; G05D 9/00; B67D 5/30
(52) U.S. Cl. .......................... 422/100; 422/105; 422/106; 422/103
(58) Field of Search .................. 422/100, 102, 422/103, 104, 105; 73/864.01, 864.11, 864.17, 864.24, 864.25, 864.35, 864.31

(56) References Cited

U.S. PATENT DOCUMENTS

| | | |
|---|---|---|
| 4,199,013 * | 4/1980 | Reich et al. ............ 414/130 |
| 4,276,260 | 6/1981 | Drbal et al. . |
| 4,326,851 | 4/1982 | Bello et al. . |
| 4,445,391 | 5/1984 | Cabrera . |
| 4,507,977 | 4/1985 | Cabrera . |
| 4,517,302 * | 5/1985 | Saros .................... 436/180 |
| 4,544,084 * | 10/1985 | Cleland ................. 222/56 |
| 4,702,889 | 10/1987 | Cabrera et al. . |
| 4,752,690 | 6/1988 | James . |
| 4,844,887 * | 7/1989 | Galle et al. ............. 422/65 |
| 4,896,546 | 1/1990 | Cabrera et al. . |
| 5,094,961 | 3/1992 | del Valle et al. . |
| 5,158,751 | 10/1992 | del Valle et al. . |
| 5,255,568 | 10/1993 | del Valle et al. . |
| 5,460,055 | 10/1995 | Parker . |
| 5,558,838 * | 9/1996 | Uffenheimer ............ 422/100 |
| 5,736,105 * | 4/1998 | Astle ..................... 422/100 |
| 5,744,099 * | 4/1998 | Chase et al. ........... 422/82 |
| 5,820,824 * | 10/1998 | Tanaka .................. 422/100 |
| 5,843,378 * | 12/1998 | El-Hage et al. ........ 422/180 |
| 5,927,547 * | 7/1999 | Papen et al. ............ 222/57 |
| 6,083,762 * | 7/2000 | Papen et al. ............ 436/180 |
| 6,100,094 * | 8/2000 | Tajima .................. 436/54 |
| 6,158,269 * | 12/2000 | Dorenkott et al. ....... 73/37 |

\* cited by examiner

Primary Examiner—Jill Warden
Assistant Examiner—Brian R Gordon
(74) Attorney, Agent, or Firm—Warren W. Kurz; Mitchell E. Alter

(57) ABSTRACT

A method and apparatus for aspirating and dispensing precise volumes of liquid, e.g. whole blood, comprises an aspiration probe or needle having an internal volume precisely equal to a desired volume to be dispensed, and a computer-controlled shear valve for trapping aspirated liquid inside the probe for subsequent dispensing. A liquid sensor positioned downstream of the shear valve cooperates with a liquid level sensor on the probe tip to assure that the probe lumen is filled with the aspirated liquid.

10 Claims, 12 Drawing Sheets

METHOD AND APPARATUS FOR ASPIRATING AND DISPENSING LIQUIDS

BACKGROUND OF THE INVENTION

1. Field of the Invention

This invention relates to improvements in methods and apparatus for aspirating a volume of liquid (e.g., whole blood) from a container (e.g., a test tube or vial) and for dispensing a precise aliquot of such volume to a work station for processing or analysis. The invention is particularly useful in the fields of hematology, flow cytometry and blood chemistry in which it is often necessary to aspirate and dispense, with high precision, relatively tiny volumes (e.g., 10–100 microliters) of blood for analysis.

2. Discussion of the Prior Art

Automated hematology instruments typically comprise apparatus for aspirating a blood sample from an open or sealed container, and for dispensing one or more precise aliquots or volumes of the aspirated sample to a workstation for analysis. In general, such liquid aspiration/dispensing apparatus is either of two types: (i) those that use blood sampling valves (BSV's) to segment an aspirated blood sample into one or more precise volumes or aliquots for subsequent dispensing; and (ii) those that use a syringe pump to "suck and spit" a precise volume of blood.

Automated hematology instruments manufactured by Beckman Coulter, Inc. (e.g., the MAXM™, STKS™ and GEN•S™ blood analyzers) employ BSV's for segmenting aspirated blood samples into multiple aliquots for analysis. When operating in a fully automated mode, these instruments operate to cause an aspirating needle to (i) puncture the respective septum's of sealed vials containing a blood sample, (ii) dip below the surface of the blood sample in the vial, and (iii) aspirate a relatively large volume (e.g., 250 mircoliters) of blood into a fluid conduit connecting the aspiration needle and a vacuum pump used to provide the negative pressure required for aspiration. Positioned within the fluid conduit some distance from the aspiration probe is the BSV assembly that serves to segment the aspirated blood into several precise aliquots of differing volumes for subsequent dispensing. The BSV typically comprises three confronting and concentrically arranged disc elements, the center element being rotatably mounted for movement with respect to the outer elements. At least one disc element defines one or more aliquoting chambers, either in the form of (i) a groove(s) formed in a planar surface thereof that confronts a similar planar surface of one of the other discs, (ii) a through-hole connecting opposing planar surfaces of one of the disc elements, and/or (iii) one or more external loops of conduit connected to such grooves and/or through holes. The physical volume of each chamber(s) is sized to be equal to that of the aliquot(s) desired. A typical volume for an aliquot of blood to be analyzed in a hematology instrument is between approximately 5 and 75 mircoliters. When the rotatable disc is in a first position, the aliquoting chamber (s) is operatively connected to the aspirated blood supply, thereby enabling blood to enter and fill the chamber(s) under a vacuum force provided by the vacuum pump. When the rotatable disc is rotated to a second position, the blood supply is sheared off from the aliquoting chamber(s), and the desired volume of blood is trapped in the chamber(s). When the rotatable disc is subsequently rotated to a third position, the trapped blood can be dispensed from the aliquoting chamber(s) and advanced to a workstation for processing or analysis. Blood sampling valves of the type described are disclosed in the commonly assigned U.S. Pat. Nos. 4,445, 391; 4,507,977; 4,702,889; 4,896,546; 5,158,751; 5,255,568; and 5,460,055.

To assure that the aliquoting chamber(s) of the BSV are filled with blood, it is common in the above instruments to position a pair of bubble detectors on opposites sides (i.e., on the upstream and downstream sides) of the valve. The detectors serve to sense that the valve is positioned within the aspirated volume of blood transported through the conduit, as well as to sense any air bubbles in the blood that would indicate that the valve chamber(s) are not full of blood at the time the rotatable disc element shears off the blood supply as it rotates to its second position. Such an arrangement is described in the commonly assigned U.S. Pat. No. 5,094,961.

When operating in a fully automated mode, hematology instruments of the above type are highly effective in quickly aspirating and dispensing precisely metered volumes of blood from a continuous supply of sealed vials. As noted above, they do require that each blood sample processed be relatively large in volume (e.g., 250 mircoliters or more) in order to enable the BSV to be located at a convenient distance from the aspirating needle. This large volume requirement can be problematic when the source of the blood sample is not large, as in the case when the blood is drawn from an infant or newborn. To enable the analysis of small, as well as other "special" blood samples, the above instruments are designed to operate in a "walk-up" mode in which a secondary aspiration probe directly coupled to the BSV (i.e., without any intervening conduit) is used to aspirate the "special" sample directly into the BSV. While this arrangement significantly reduces the blood volume requirement, it still requires that the probe itself be filled before any sample reaches the BSV for segmentation. Also, the secondary probe is not adapted to aspirate blood from sealed vials. Thus, in the "walk-up" mode, an operator must manually present an open vial sample to the secondary aspiration probe and visually assure that the probe tip is sufficiently below the level of blood in the vial as not to aspirate any air into the BSV's aliquoting chambers. This manual involvement is disadvantageous in that it reduces the throughput of the instrument.

As regards the syringe pump approach for aspirating and dispensing liquid, this approach requires precision movement of a plunger or diaphragm to move in a fluid circuit. As the plunger or diaphragm moves in a first direction, a negative pressure (vacuum) is created in an aspiration probe, thereby causing liquid to be sucked into the probe and its associated liquid conduit through the probe tip. As the plunger or diaphragm moves in the opposite direction, a positive pressure is created in the circuit, causing any liquid in the circuit to be ejected (dispensed or "spit") through the probe tip. Obviously, the accuracy of this apparatus depends on the accuracy of movement of the moving member. While this apparatus is advantageous from the standpoint that it can aspirate and dispense very small volumes of liquid (since no conduit needs to be filled before aliquoting can occur, as is the case of the aforementioned BSV apparatus, it is less accurate than the BSV apparatus since the volume of liquid aspirated/dispensed relies entirely on the repeatability of the plunger/diaphragm movement. Typically, the accuracy of a syringe pump apparatus can vary by as much as 1–5 mircoliters between successive actuations.

SUMMARY OF THE INVENTION

In view of the foregoing, an object of the present invention is to provide an improved liquid aspiration/dispensing apparatus of the type described, an apparatus that is improved at least from the standpoint that it provides both the accuracy of the aforementioned BSV apparatus and the low volume feature of the aforementioned syringe pump apparatus.

The liquid aspirating/dispensing apparatus of the invention basically comprises:

(a) an aspirating probe (or needle) having a tubular housing with a proximal end and a distal end adapted to access a liquid in a container, the tubular housing having an internal volume substantially equal to a desired predetermined volume of liquid to be ultimately dispensed;

(b) aspiration means for causing liquid in the container to enter the distal end of the aspirating probe and to completely fill the tubular housing, whereby the aspirating probe contains a desired predetermined volume of liquid;

(c) sensing means for sensing that the tubular housing is completely filled with aspirated liquid, said sensing means comprising (i) a first liquid detector for sensing aspirated liquid that has passed completely through the aspirating probe, and (ii) a second liquid detector for sensing that the distal end of the aspirating probe has remained in the contained liquid during aspiration;

(d) means operatively coupled and responsive to the sensing means for trapping aspirated liquid in the aspirating probe, such trapping means comprising a shear valve operatively connected to the proximal end of aspirating probe, and (e) means for dispensing the trapped aspirated liquid from the distal end of said aspiration probe.

In a preferred embodiment of the inventions the first liquid detector comprises a photoelectric detector or the like, for sensing aspirated liquid that has passed completely through the aspirating probe, and the second sensing means comprises a second liquid detector, e.g., capacitance or ultrasonic detector, connected to the distal end of the aspirating probe for detecting liquid in the container.

One consequence of the invention is the ability to vary the desired volume of the dispensable liquid by simply changing the aspirating probe to one having a greater or lesser volume. In addition, the invention overcomes the inaccuracy deficiency of prior art apparatus that depend on positive displacement (syringe) pumps for aspiration purposes. In particular, by using the tubular housing of the aspirating probe as a means for metering the sample, there can be no variation of the amount of liquid that can be dispensed. Also, compared to the aforementioned BSV apparatus, the total volume of blood needed to dispense a precise volume is minimal owing to the total elimination of any conduit between the aspirating probe tip and the aliquoting chamber of the apparatus.

The invention will be better understood from the ensuing description of preferred embodiments, reference being made to the accompanying drawings.

DETAILED DESCRIPTION OF PREFERRED EMBODIMENTS

Figure 1:
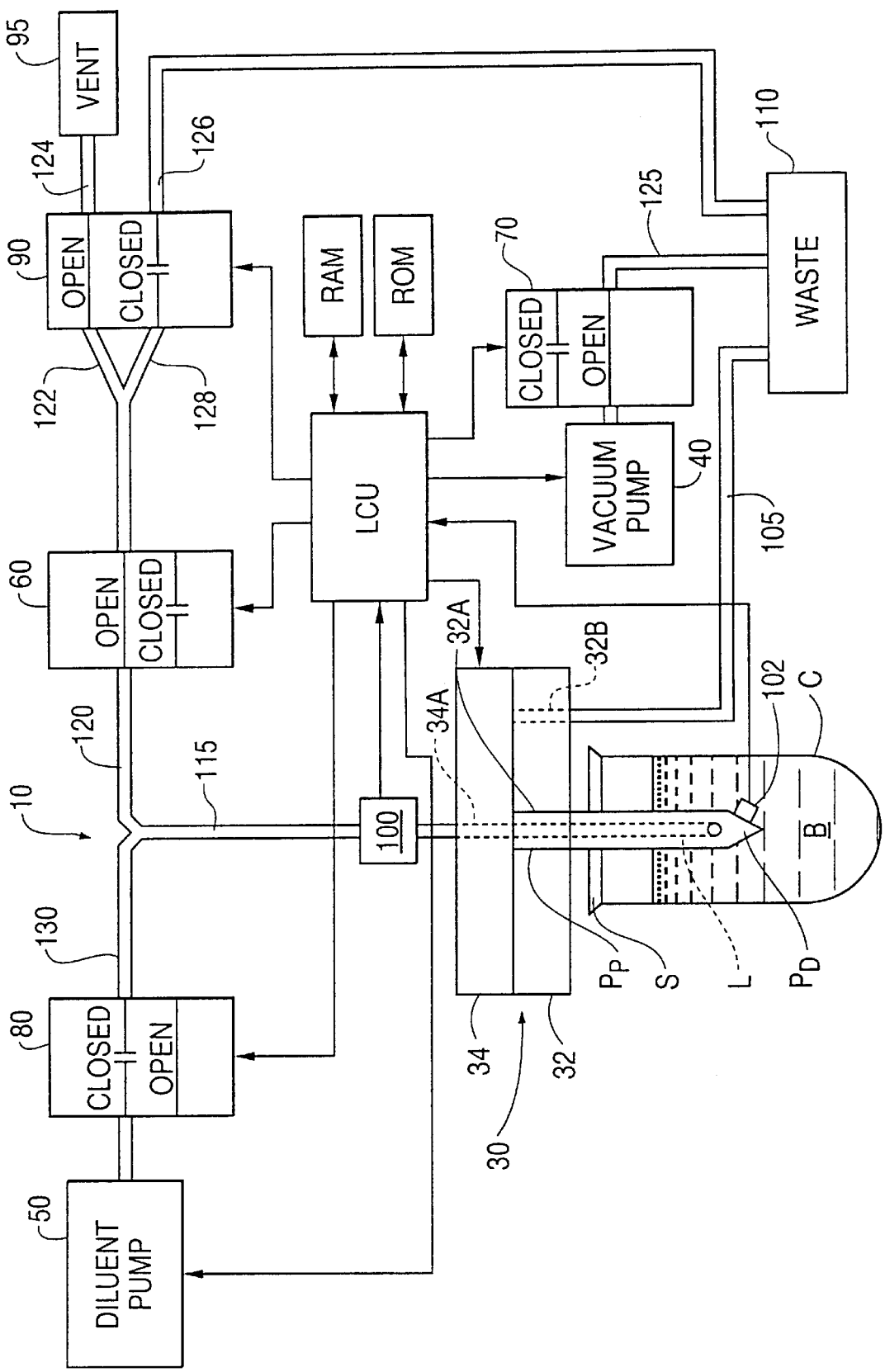
FIG. 1 is a schematic illustration of a liquid aspirating/dispensing apparatus embodying the invention, such apparatus being shown in a container-venting mode.

Referring now to the drawings, FIG. 1 schematically illustrates the basic components of a preferred liquid aspirating and dispensing apparatus 10 embodying the present invention. Such apparatus is generally adapted to aspirate a liquid such as whole blood B from a container C and to subsequently dispense a precise volume of such liquid to a work station or the like (e.g., a mixing chamber of an instrument adapted to analyze the dispensed sample). As will be more apparent from the following description, the precise volume of the liquid to be dispensed is defined by the internal volume of the lumen L of a needle or probe P used to aspirate the sample. In this preferred embodiment, operation of the apparatus is computer-controlled, the apparatus operating in response to commands produced by a suitably programmed logic and control unit (LCU), such as a conventional microprocessor and its associated read-only memory (ROM) and random access memory (RAM). As will be further explained below, the LCU acts to control the operation of (i) a shear valve assembly 30 to which the aspiration probe is directly connected: (ii) a vacuum pump 40 used to selectively create a negative pressure in the aspiration probe; (iii) a diluent pump 50 used to introduce a suitable diluent into the apparatus for the purpose of expelling (i.e., dispensing) aspirated liquid from the aspiration probe, and/or cleansing the aspiration probe, the shear valve assembly and associated conduits of aspirated liquid between successive cycles; (iv) a plurality of pinch valves 60, 70 and 80 used to selectively couple the aspiration probe to the vacuum and diluent pumps; and (v) a double-acting pinch valve 90 used to selectively connect the aspiration probe to either a vent 95 for equilibrating the pressure in the liquid container, or to the vacuum pump 40. In providing its control signals to the aforementioned components, the LCU responds to input signals provided by a photoelectric liquid detector 100 used to detect aspirated liquid that has passed through the shear valve assembly, and a liquid level sensor 102 used to detect that the distal end of the aspirating probe is safely below the level of liquid in the container C.

Essential to the effective operation of the invention is a means for trapping or retaining liquid within the aspiration probe after aspiration has taken place. According to a preferred embodiment, such liquid-trapping means takes the form of the shear valve connected directly to the proximal end $P_p$ of the aspiration probe. The shear valve preferably comprises a pair of confronting ceramic plates 32, 34, each preferably being circular or disc shaped and concentrically arranged with respect to the other. The plates are each about 6 mm thick and are slidably movable (e.g., rotatable) with respect to each other so that a bore hole 34A formed in plate 34 can be made to selectively align with either of a pair of bore holes 32A and 32B formed in plate 32. Alternatively, the shear valve can comprise a pair of confronting rectangular plates that move linearly with respect to each other to align respective bore holes in each.

Figure 2:
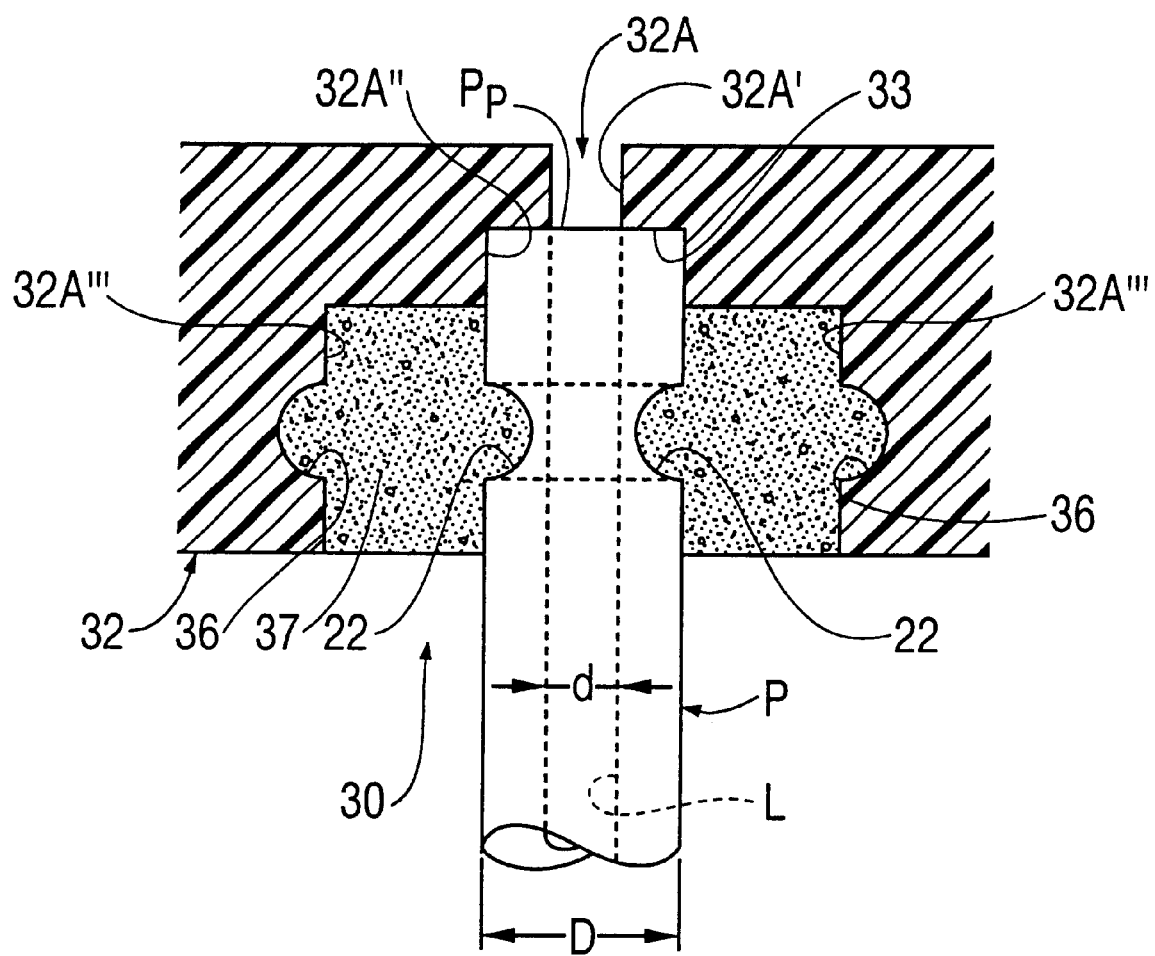
FIG. 2 illustrates a preferred coupling between the aspiration probe and the shear valve assembly of the FIG. 1 apparatus.

Referring to FIG. 2, the bore hole 32A formed in shear valve plate 32 releasably supports the proximal end $P_p$ of the aspiration probe P. As shown, bore hole 32A is of three different diameters measured along its length. A first portion 32A' of the bore hole has a diameter substantially equal to the inside diameter d of the lumen L of aspiration probe, thereby providing an unimpeded and smooth path for aspirated liquid to pass through the probe/shear valve interface 33. A second portion 32A" of the bore hole 32A has a diameter substantially equal to the outside diameter of the probe, whereby a press fit is provided between such portion of the bore hole 32A and the proximal portion of the probe. A third portion 32A''' of the bore hole 32A has a diameter substantially larger than the outside diameter of the probe and is adapted to receive a suitable adhesive 37, e.g., an epoxy resin, which serves to secure the probe to the valve plate. Preferably, the circumferential outer wall of bore hole portion 32A''' is provided with a groove 36 similar in shape to that of a groove 22 formed in the outer wall of the distal portion of the probe, such grooves cooperating to retain the probe-bonding material in place. Referring to FIG. 1, the second bore hole 32B formed in valve plate 32 is adapted to be connected to a liquid conduit 105 which, in turn, can be connected to a drain 110, as explained below. The respective diameters of bore holes 32B and 34A, and bore hole portion 32A' are substantially equal. Bore hole 34A of the valve plate 34 is connected to a liquid conduit 115, which, as explained below, conveys liquid to and from the shear valve.

Figure 3:
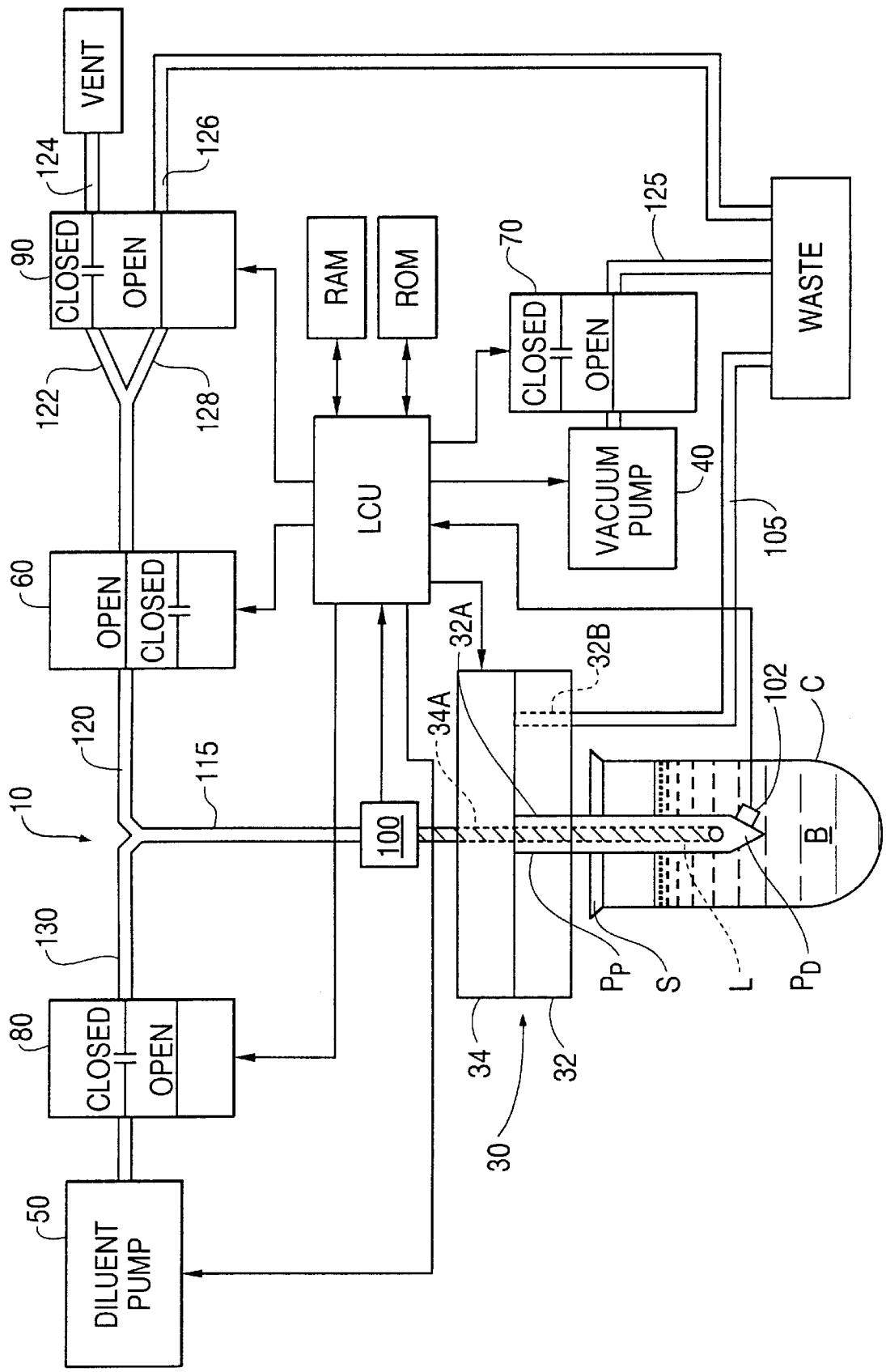
FIG. 3 is a schematic illustration of the FIG. 1 apparatus showing the components in a liquid aspirating mode.
Figure 4:
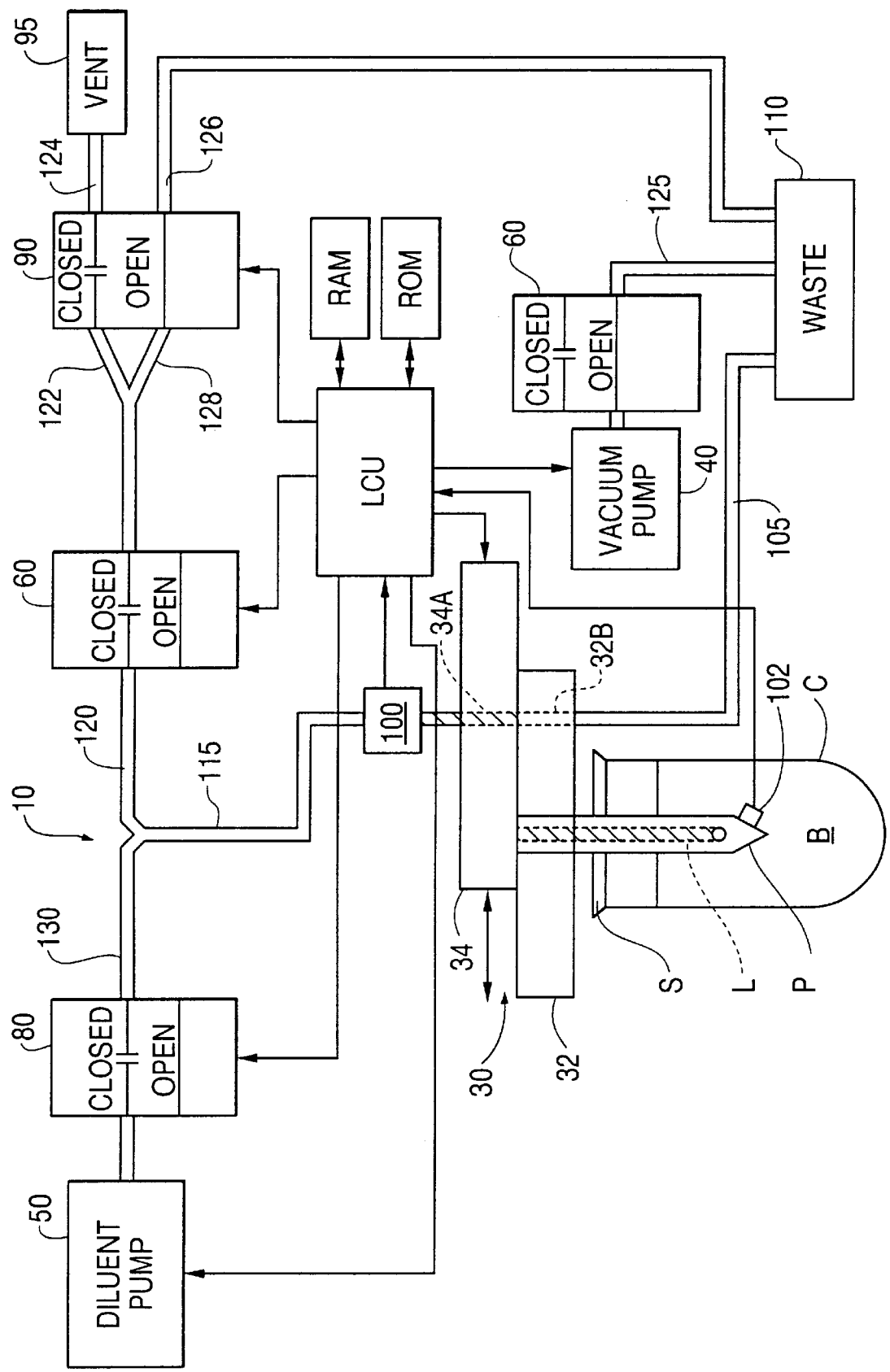
FIG. 4 is a schematic illustration of the FIG. 1 apparatus showing the components in a liquid segmenting mode.
Figure 5:
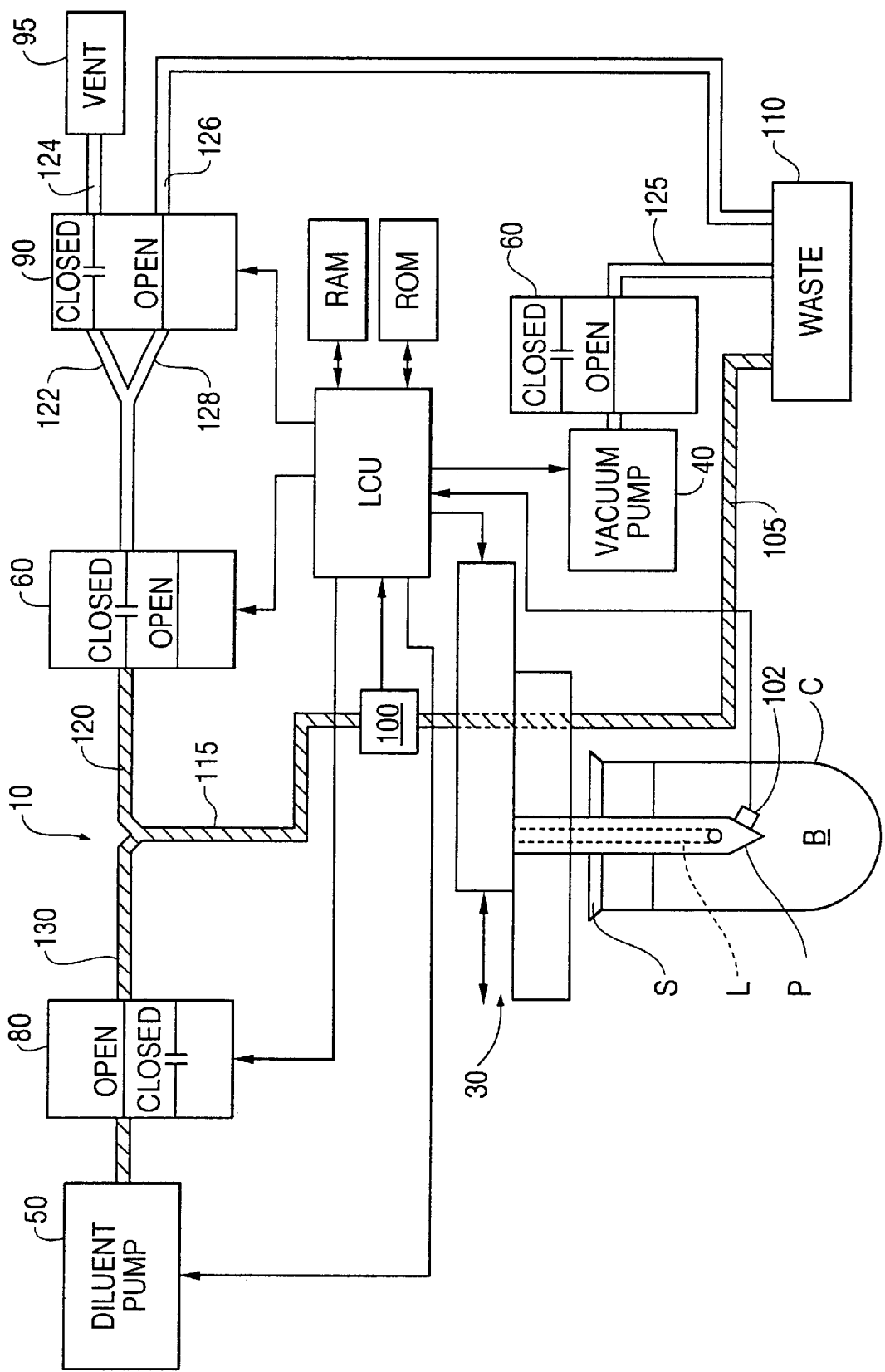
FIG. 5 is a schematic illustration of the FIG. 1 apparatus showing the components thereof in a probe-cleaning mode.

The FIG. 1 apparatus is best described in terms of its operation, reference being made to FIGS. 3–5 as well. It is assumed that the liquid container C is capped by a thin, pliable seal or septum S, such as a rubber cap, which can be punctured by the tapered distal end $P_D$ of the aspiration probe as it enters the container. Obviously, the apparatus is shown as being oversized with respect to the container for illustrative purposes. As explained in more detail below, the apparatus is programmed to carry out the following sequence of steps: (a) venting of the container; (b) aspirating of the sample in the container; (c) segmenting the aspirated sample within the aspiration probe; (d) cleansing or rinsing the shear valve and associated conduits for subsequent use; (e) dispensing the segmented sample; and (f) purging the aspiration probe, shear valve and all associated conduits of all liquids prior to subsequent use.

Venting: Referring to FIG. 1, prior to puncturing the container seal S, pinch valve 60 and 80 are "CLOSED" (i.e., OFF), thereby isolating the probe interior from all fluid circuit elements. At this time, pinch valve 70 is OPEN, and the state the double-acting pinch valve 90 is as shown in FIG. 1, i.e., valve 60 is connected to vent 95 and disconnected from the waste chamber 110 and the vacuum pump 40 which, when activated, draws a vacuum through the waste chamber. All conduits are void of any liquids as a result of a purging step discussed below. Upon puncturing the container seal, the probe is advanced into the container to a level at which the level sensor 102 carried by the probe tip signals that the tip is safely beneath the level of liquid to be aspirated. Upon receiving this signal, the LCU acts to open pinch valve 60, thereby venting the interior of the container C to the atmosphere through vent 95. Such venting is effected through the shear valve 30, pinch valves 60 and 90 and through conduits 115, 120, 122 and 124 which communicate with the vent. As noted, the venting operates to equalize the pressure inside the container with that of atmosphere.

Aspiration: Upon venting the container, the LCU operates to reverse the state of double-acting pinch valve 90, thereby obstructing fluid communication between vent 95 and the sealed container, and permitting fluid communication between the vacuum pump 40 and the sealed container. Pinch valves 60 and 70 remain OPEN, and pinch valve 80 remains CLOSED. See FIG. 3. Upon receiving a signal from level sensor 102 indicating that the probe tip is below the level of the contained liquid, the LCU activates vacuum pump 40 to begin aspiration of blood B through the aspirating probe; aspiration occurs, of course, as a result of the negative pressure within the probe provided by vacuum pump 40 applied through conduits 125, 126, 128, 120 and 115. Alternatively, a diaphragm pump or any other means for creating a pressure differential in the system, can replace the vacuum pump 40. Level sensor 102 may be of the type disclosed, for example, in the commonly assigned U.S. Pat. Nos. 4,276,260 and 4,326,851. Upon entering the probe, the aspirated blood will proceed to fill the probe lumen L and continue up through shear valve 30, into conduit 115 and eventually past the liquid detector 100 positioned in conduit 115. The liquid detector, which may be, for example, of the type disclosed in the commonly assigned U.S. Pat. No. 4,752,690, is closely spaced to the shear valve, on the downstream side thereof. The closer the spacing the better, since the volume of blood in the conduit between the shear valve and the detector, as well as any blood in the bore hole of valve plate 34 will not be used (i.e., dispensed) and is eventually drained to waste. Preferably, the spacing is such that less than 10 mircoliters of liquid is required to reach the liquid detector. At the moment the aspirated blood sample passes the liquid detector, the detector will transmit an electrical signal to the LCU, signaling that further aspiration is to cease.

Segmenting: Upon receipt of a signal from detector 100, the LCU will close pinch valve 60 and disable the vacuum source 40. Referring to FIG. 4, the LCU will then send an electrical signal to shear valve 30 instructing it to rotate plate 34 so as to effectively trap the aspirated liquid inside the probe lumen in preparation for dispensing to a work station. The blood is retained in the probe by the external atmospheric forces. The aspiration probe is then removed from the liquid container and is positioned relative to a workstation to dispense the trapped blood.

Cleansing: Before dispensing the metered sample to a work station or the like, the invention contemplates the removal of any excess aspirated liquid (blood) from within the shear valve plate and the conduit 115. The removal of such liquid is accomplished by rotating plate 34 of shear valve 30 so that bore holes 32B and 34A align (as shown in FIGS. 4 and 5), thereby providing a fluid path to a waste chamber 110 via conduit 105. Referring to FIG. 5, the excess aspirated liquid is removed by closing pinch valve 60, opening pinch valve 80, and introducing a predetermined amount of diluent or solvent from the diluent pump 50 into conduits 130 and 115. The entering diluent operates to push the excess aspirated liquid to the waste chamber, through the aligned bore holes 32B and 34A. After removing the excess liquid in the manner described, the aspiration probe is moved to a dispensing position.

Figure 6:
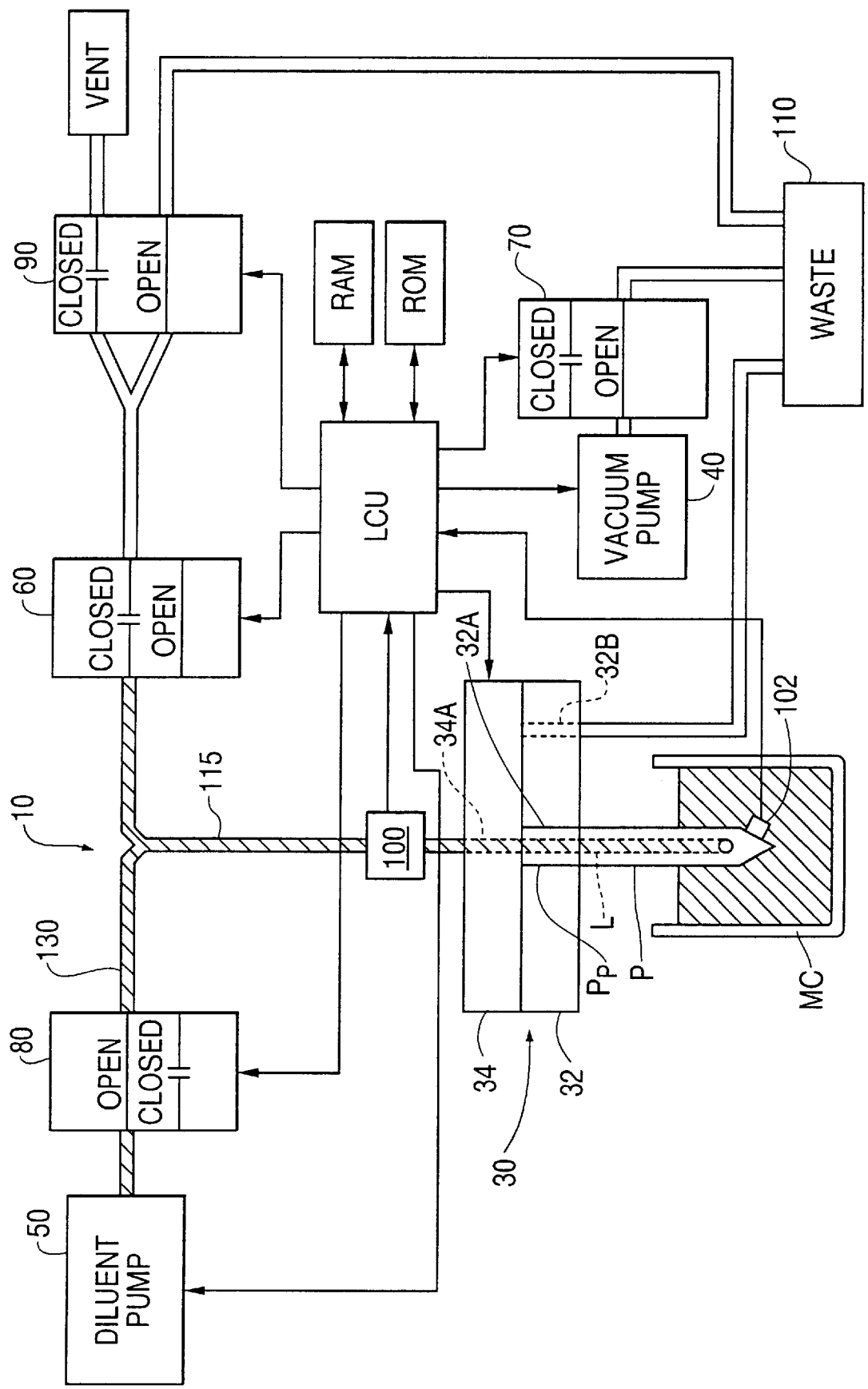
FIG. 6 is a schematic illustration of the FIG. 1 apparatus showing the components thereof in a liquid dispensing mode.

Dispensing: To dispense the trapped liquid in the aspiration probe, the LCU operates to rotate plate 34 of the shear valve back to the FIG. 1 position in which bore hole 34A is again in fluid communication with the interior lumen of the probe. See FIG. 6. At this point, pinch valve 80 is still open and pinch valve 60 is still closed. The LCU then activates the diluent pump 50 so that a predetermined volume of diluent is pumped into conduits 130 and 115. The force of the pumped diluent causes the aspirated and segmented liquid in the probe lumen to be dispensed therefrom. When using the aspirating/dispensing apparatus of the invention in a blood analyzing instrument, it is normally desired to dilute the dispensed sample, perhaps by as much as 1000:1. This can be easily effected in a mixing chamber MC by continuing the flow of diluent after the aspirated blood sample has been dispensed. As indicated by the double cross-hatching in the mixing chamber MC of FIG. 6, the aspirated liquid in the probe has been diluted with diluent provided by pump 50. This has the added effect of rinsing the probe interior for subsequent use.

Figure 7:
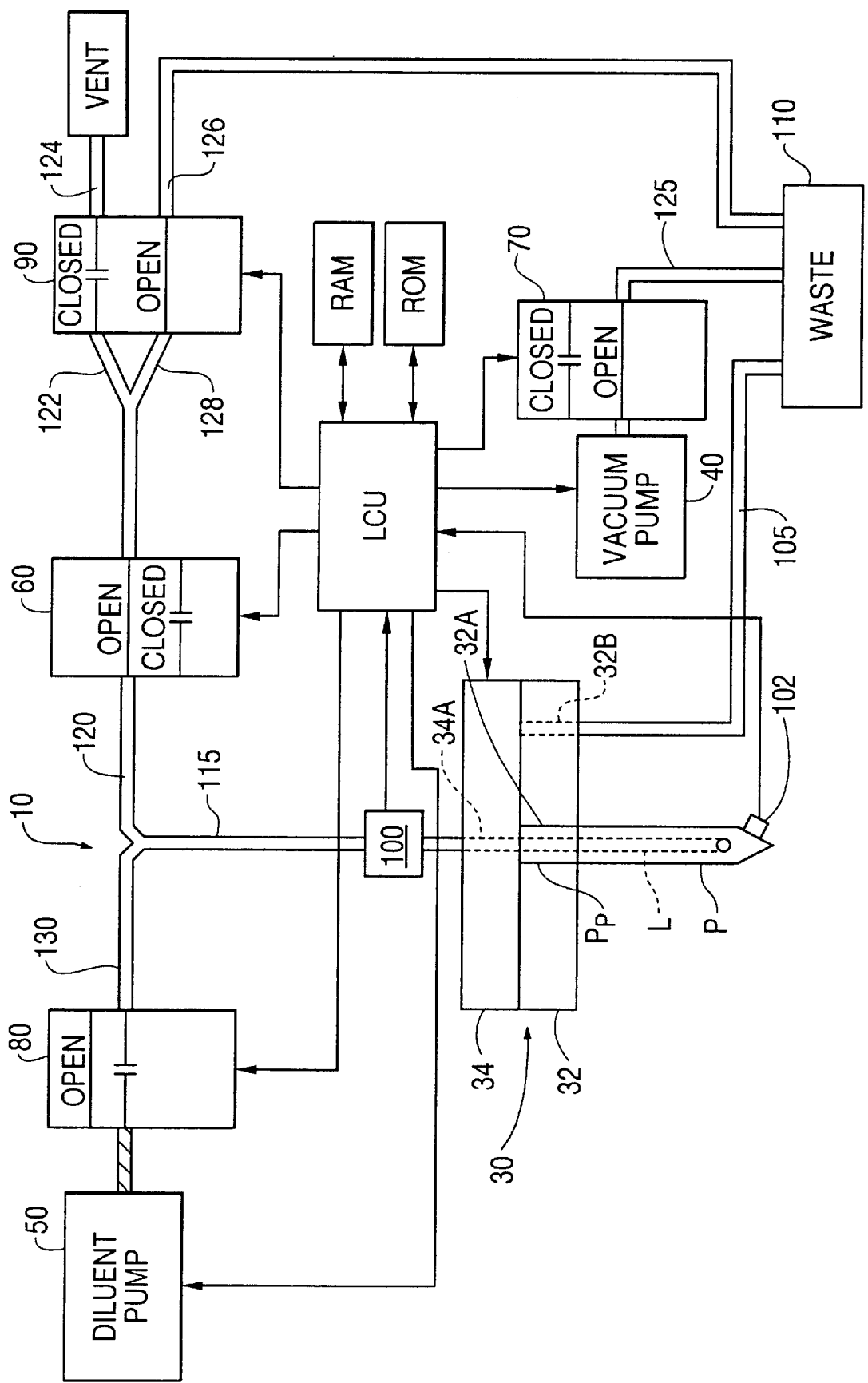
FIG. 7 is a schematic illustration of the FIG. 1 apparatus showing the components thereof in a liquid purging mode.

Purging: After the liquid within the probe has been dispensed and, if desired, diluted, it is desirable to purge any traces of the metered liquid and the remaining diluent present within the interior of the probe so as to prevent contamination of the succeeding aspirated sample. To accomplish this purging, the aspiration probe is removed from the workstation and exposed to ambient air. Then, referring to FIG. 7, the LCU operates to (i) close pinch valve 80, thereby cutting off the supply of diluent; (ii) open pinch valve 60, thereby coupling the aspiration probe to the vacuum source through valves 90 and 70 which are already in its vacuum-coupling state; and (iii) activate the vacuum pump 40 to aspirate and thereby remove any residual liquid from within the probe, shear valve and associated conduits. This residual liquid proceeds to waste 110 under the force of the vacuum pump.

The above-described aspirating process presupposes the pressure inside the sealed container during piercing and prior to ventilation is less than atmospheric pressure. In the event that the pressure inside the container is greater than atmospheric pressure, it may be appreciated that the higher pressure may cause liquid to enter the aspiration probe and associated conduits during ventilation. If the pressure within the container is high enough to cause blood to rise past liquid detector 100, then initiation of the aspiration process by vacuum is not required. Instead, the flow of blood past detector 100 indicates that the probe lumen is filled with blood, and is therefore ready to be dispensed. At this point, the LCU signals valve 60 to shut off communication between vent 110 and the sealed container and instructs shear valve plate 34 to rotate to the FIG. 4 position so as to segment liquid within the probe, and to provide for fluid communication between the diluent source 50 and drain 110 to permit removal of excess aspirated liquid present in shear valve 30 and conduit 115.

In achieving the above-noted blood aspirating process, it is preferred to use a single lumen aspirating probe of the type shown in FIG. 1. As noted, the internal volume of the probe lumen should be precisely equal to that of the desired liquid sample to be dispensed; consequently, this characteristic of the invention allows the operator to vary the desired dispensable sample volume by simply changing the probe to one having an internal lumen volume equal to the desired sample volume.

Figure 8:
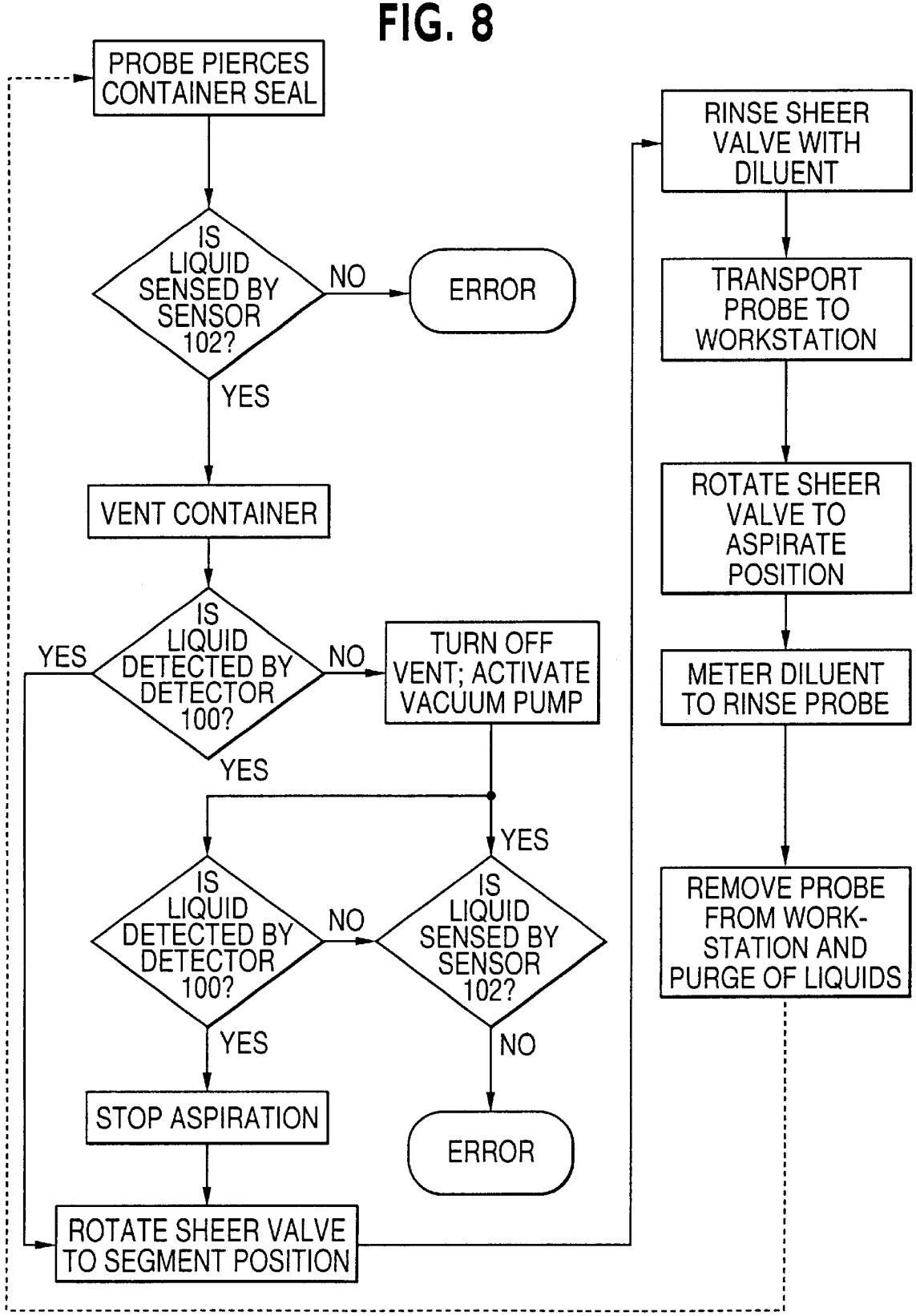
FIG. 8 is a flowchart illustrating a preferred sequence of operations carried out by the programmable logic and control unit comprising the preferred embodiment of the invention.

FIG. 8 discloses a flowchart illustrating a preferred program carried out by the LCU and its respective ROM and RAM components. The LCU is programmed so that prior to the probe piercing the sealed container, valves 60 and 80 are closed, i.e., no fluid flow, and valve 70 is positioned such that conduits 122 and 124 are in fluid communication and conduits 128 and 126 are not. Once the probe pierces the sealed container, the LCU is programmed as follows: first, it is determined whether there is liquid (e.g., blood) in the sealed container to aspirate. This information is provided by liquid level sensor 102 located on the distal end of the probe; if liquid is not sensed, an error signal is generated and the apparatus is shut down by the LCU. If the level sensor detects liquid in the container, the apparatus proceeds to vent the interior of the sealed container to the atmosphere. This is achieved by opening pinch valve 60. During ventilation, liquid detector 100 senses the presence of liquid flow through conduit 115. If flow is sensed by detector 100, then the LCU operates to close valve 60 and rotate plate 34 of shear valve 30 in preparation for dispensing of the liquid sample to the workstation. However, if no flow is sensed after a predetermined period of time, the LCU operates to switch the state of double-acting valve 90 such that conduits 122 and 124 are no longer in fluid communication and, instead, fluid communication is established between conduits 128 and 126. The LCU proceeds to instruct vacuum pump 40 to begin aspiration of liquid from the sealed container. As indicated above, the vacuum pump operates through waste chamber 110 and pinch valve 70 to draw a vacuum in conduit 126. Throughout aspiration, liquid level sensor 102 continuously checks for the presence of air bubbles within liquid entering through the distal end of the probe. If air is detected within the incoming liquid, then the LCU shuts down the aspiration process and an error is indicated; otherwise, aspiration proceeds until liquid detector 100 detects the flow of blood through conduit 115.

Once blood flow is detected past liquid detector 100, the LCU instructs vacuum pump 40 to cease aspiration and directs the rotation of plate 34 of shear valve 30 so as to segment or trap blood within the probe lumen. Now, the LCU operates to open valve 80 and to close valve 60, and it instructs diluent pump 50 to introduce a predetermined volume of diluent into conduits 130 and 115 so that excess aspirated blood sample may be rinsed from within shear valve 30 and conduit 115 through the aligned bore holes 34A and 32B in the shear valve. At this point, the LCU initiates transport of the probe to the dispense site. Upon arrival, the LCU directs rotation of plate 34 back to its original position such that aspirated liquid trapped within the probe may be flushed into a dispense container. To do this, the LCU instructs the diluent pump 50 to release a predetermined volume of diluent which flows into the probe, and proceeds to flush the sample from the probe's lumen. Next, the probe is removed from the dispense site and the LCU instructs vacuum pump 40 to begin aspiration of any residual liquid present in the system. The entire circuit, being purged of liquid is now ready for another aspiration/dispense cycle.

Figure 9:
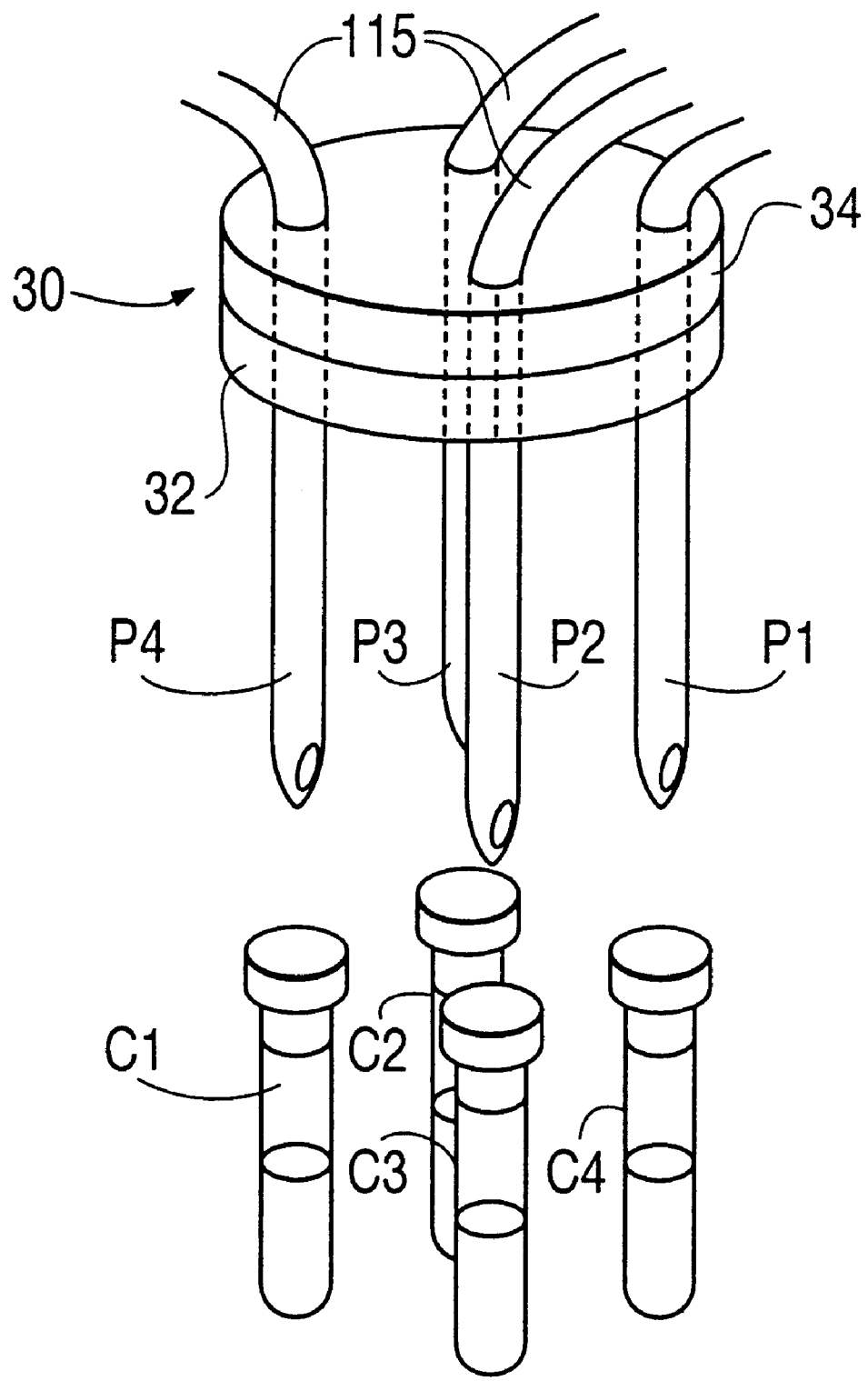
FIG. 9 schematically illustrates multiple aspirating probes connected to a single shear valve.

FIG. 9 illustrates a variation of the aforedescribed apparatus in which multiple aspiration probes P1–P4 are coupled in the manner described to a single shear valve V. This arrangement allows for the simultaneous aspiration of sample from multiple sample containers C1–C4, thereby increasing the throughput of the apparatus. Alternatively, the aspiration probes can have different internal volumes, all aspirating simultaneously from the same (or different) container(s) and each dispensing a different volume defined by its unique internal volume.

Figure 10:
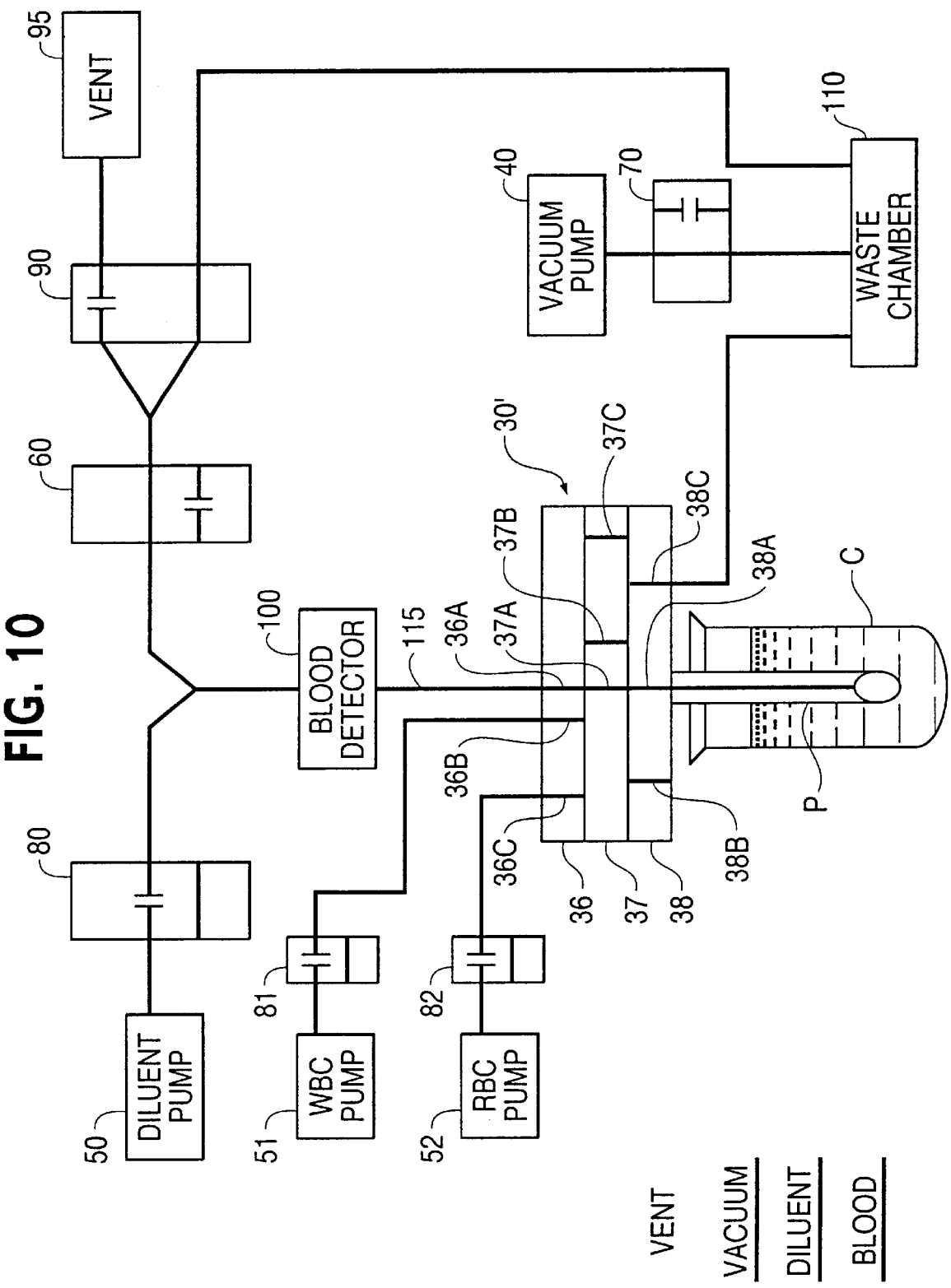
FIGS. 10–12 illustrate a hybrid aspiration/dispense apparatus in which an aliquoting blood-sampling valve is used in combination with the aliquoting probe of the invention.
Figure 11:
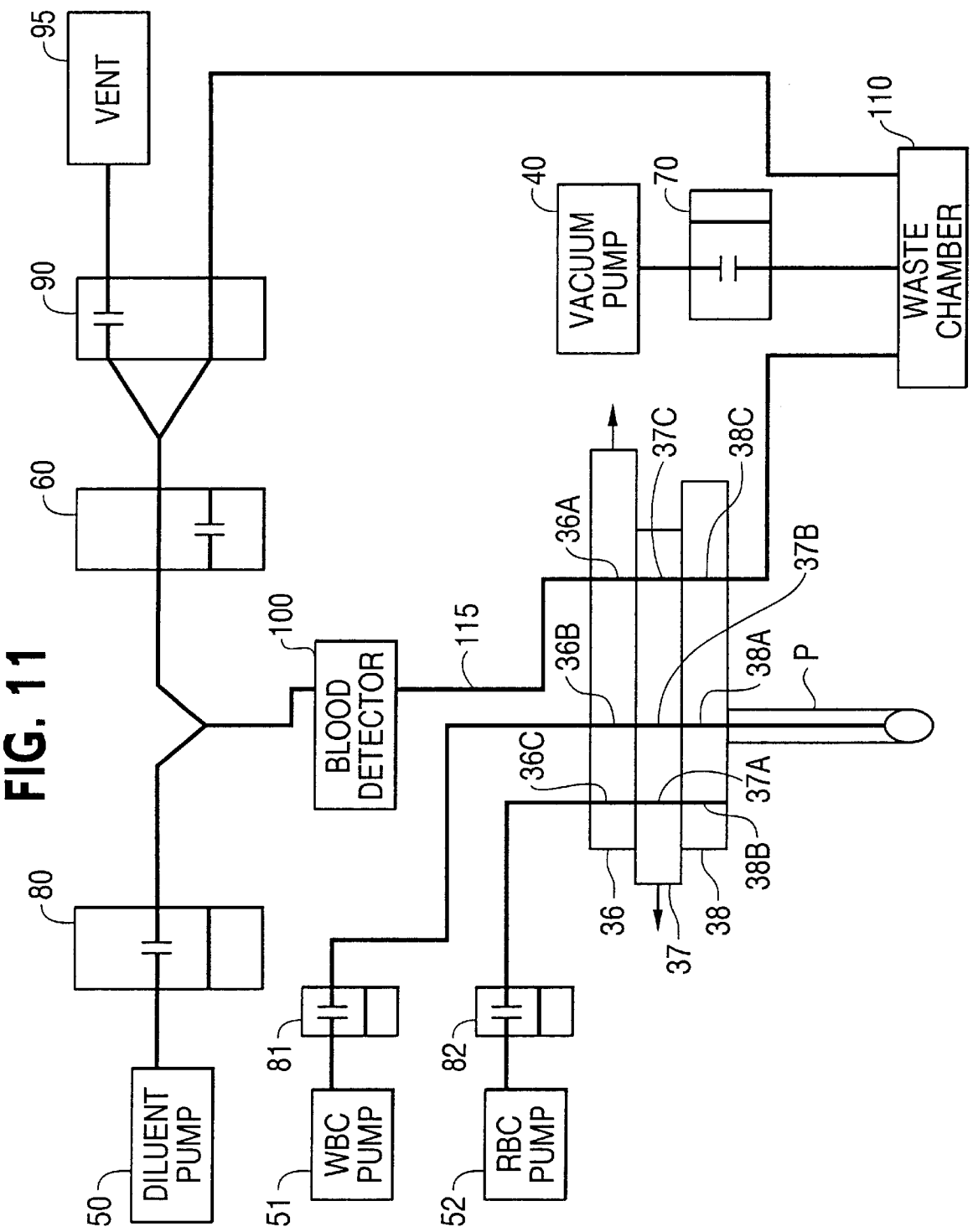
Figure 12:
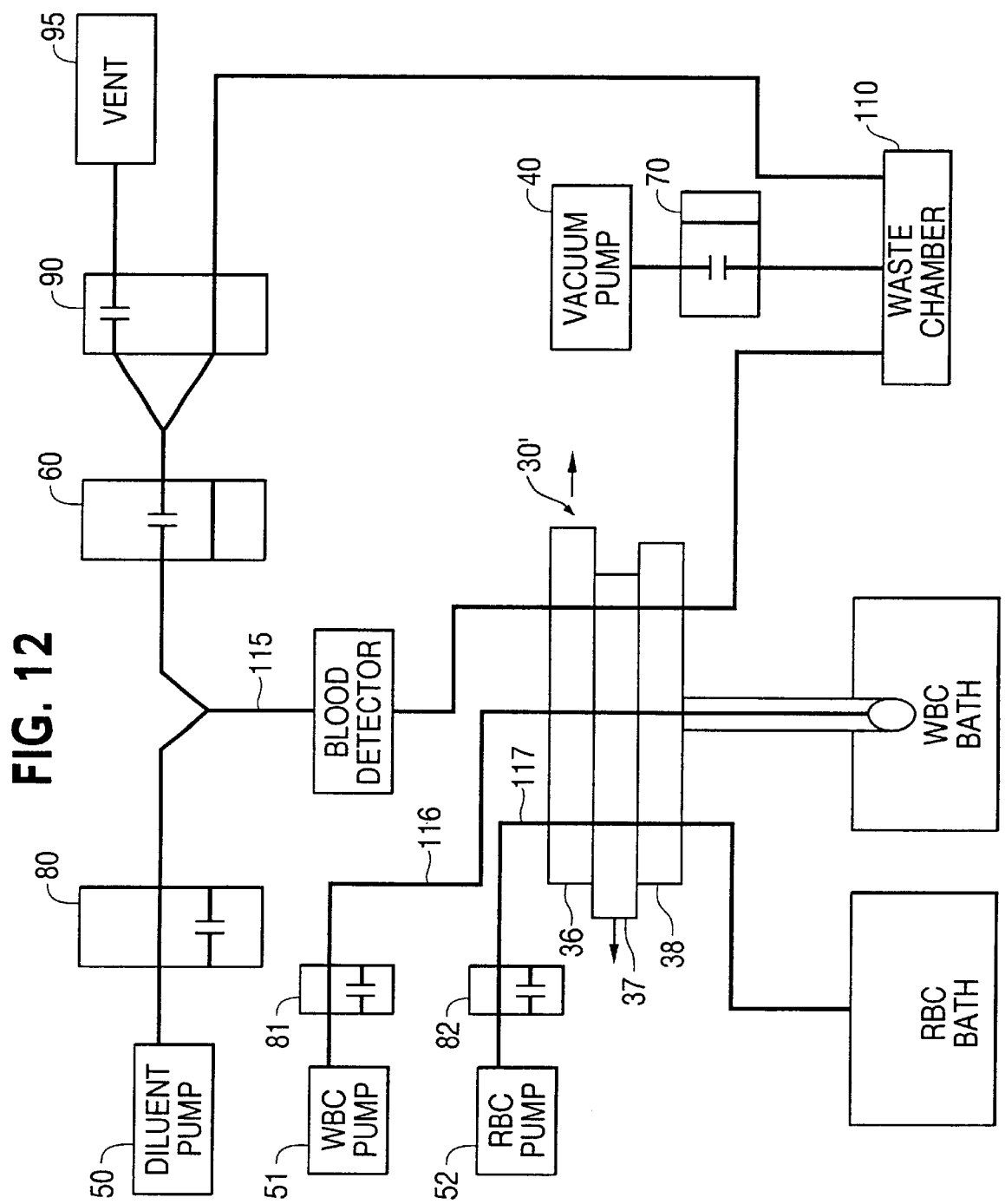

In FIGS. 10–12, a "hybrid" liquid aspirating/dispensing apparatus is illustrated that combines the aliqoting features of a conventional blood-sampling valve with the aliquoting probe of the invention. To the extent the apparatus in FIGS. 10–12 is identical to that illustrated in FIG. 1, the same reference characters are used. In contrast with the apparatus described above, the apparatus of FIGS. 10–12 employs a three plate shear valve assembly 30', such assembly comprising the plates 36, 37 and 38. As in the case of the aforedescribed shear valve 30, the lowermost plate 38 supports the proximal end of the aspiration probe P. The middle plate 37 functions, as explained below, to contain a predefined aliquot of the aspirated liquid for subsequent dispensing. During the aspiration phase, the bore holes 36A, 37A and 38A formed in plates 36, 37 and 38, respectively, are in alignment with each other, thereby providing a fluid path to the blood detector 100 in conduit 115. Assuming the liquid in container C is whole blood, it is often desirable to dispense a relatively large aliquot of whole blood for white cell analysis, and a considerably smaller aliquot of whole blood for red cell analysis. Following aspiration of the whole blood sample through the probe and upwards into conduit 115, the shear valve is actuated to segment the aspirated blood. Referring to FIG. 11, the three shear valve plates move relative to each other, whereby the relatively small volume of blood aspirated into the bore hole 37A comes into fluid communication with bore holes 36C and 38B formed in plates 36 and 38, respectively. In this position, it is ready to be dispensed for red cell analysis. At the same time, the blood aspirated into shear valve plate 36A and conduit 115 comes into fluid communication with bore holes 37C and 38C formed in plates 37 and 38, respectively. In this position, the shear valve and conduit are ready for rinsing by diluent provided by the diluent pump 50. As described above, the aspiration probe itself operates to aliquot a precise volume of blood for subsequent dispensing, and this relatively large aliquot (compared to that contained by plate 37), is subsequently used for white cell analysis.

Referring to FIG. 12, the apparatus operates to dispense the segmented blood samples by opening pinch valves 51 and 52 and activating the WBC pump 51 and RBC pump 52. Pump 51 meters a predetermined amount of lysing reagent into line 116, thereby dispensing the blood sample captured in the aspiration probe into the WBC bath. At the same time, or in sequence, the RBC pump meters a predetermined volume of diluent into line 117, thereby dispensing the aliquot captured in plate 37 into the RBC bath. The dispensed samples are diluted in their respective baths based upon the volume of fluid metered by the pumps. Meanwhile, conduit 115 and bore holes 36A, 37C and 38C are rinsed by activating the diluent pump 50.

From the foregoing description, it will be appreciated that an improved liquid aspirating and dispensing apparatus has been provided. Such apparatus is advantageous vis-à-vis the aforementioned BSV apparatus in that it requires considerably less volume of sample to operate. Compared to the syringe-pump approach, the apparatus of the invention dispenses more accurate and repeatable volumes of liquid.

The invention has been described with reference to certain preferred embodiments but it will be appreciated that variations and modifications can be effected without departing from the spirit of the invention. Such variations and modifications are intended to fall within the scope of the appended claims.

What is claimed is:

1. Apparatus for aspirating a volume of liquid from a container and for subsequently dispensing a desired predetermined volume of the aspirated liquid, said apparatus comprising:

(a) at least one aspiration probe having a tubular housing with a proximal end and a distal end adapted to access a liquid in a container, the tubular housing having an internal volume substantially equal to said desired predetermined volume of liquid to be dispensed;

(b) aspiration means for causing liquid in the container to enter the distal end of the aspiration probe and to completely fill the tubular housing, whereby the aspiration probe contains said desired predetermined volume of liquid;

(c) sensing means for sensing that the tubular housing is completely filled with aspirated liquid, said sensing means comprising (i) a first liquid detector for sensing aspirated liquid that has passed completely through the aspirating probe, and (ii) a second liquid detector for sensing that the distal end of the aspirating probe has remained in the contained liquid during aspiration;

(d) means operatively coupled and responsive to the sensing means for trapping aspirated liquid in the aspirating probe, said trapping means comprising a shear valve operatively connected to the proximal end of aspirating probe; and (e) means for dispensing the trapped aspirated liquid from the distal end of said aspiration probe.

2. The apparatus as defined by claim 1 wherein said shear valve comprises first and second plates arranged in contiguous relationship, each plate having a pair of opposing planar faces and a bore hole therebetween to enable liquid flow through said plate, said first and second plates being slidably movable relative to each other for movement between a first position in which their respective bore holes are aligned so as to enable aspiration of a blood sample from said container through said valve, and a second position in which the respective bore holes in said plates are misaligned so as to prevent liquid flow through said valve and to trap aspirated liquid within said tubular housing of said aspiration probe.

3. The apparatus as defined by claim 1 wherein said second plate further comprises a second bore hole for enabling the extraction of liquid within said bore hole of said first plate, said second bore hole being aligned with said bore hole of said first plate when said first and second plates are in said second position relative to each other, said second bore hole of said second plate being connected to a drain which is further connected to said vacuum source.

4. The apparatus as defined by claim 1 wherein the distal end of said aspiration probe is tapered and adapted to pierce a seal on said container.

5. The apparatus as defined by claim 1 wherein said means for causing liquid in said container to enter the distal end of said aspiration probe and to completely fill said tubular housing comprises a vacuum source connected to said aspiration probe for providing a negative pressure within said tubular housing of said aspiration needle relative to pressure within said sealed container.

6. The apparatus as defined by claim 1 wherein said means for causing liquid in said container to enter the distal end of said aspiration probe and to completely fill said tubular housing further comprises ventilation means selectively connectable to said aspiration probe for equilibrating the pressure inside said sealed container to atmospheric pressure.

7. The apparatus as defined by claim 1 wherein a plurality of aspiration probes are operatively connected to said shear valve for simultaneously aspirating a plurality of predetermined volumes of liquids form one or more containers, each of said plurality of aspiration probes having an internal volume substantially equal to the desired volumes of liquid to be dispensed.

8. Apparatus for aspirating a volume of liquid from a container and for subsequently dispensing at least two desired predetermined volumes of the aspirated liquid, said apparatus comprising:

(a) an aspiration probe having a tubular housing with a proximal end and a distal end adapted to access a liquid in a container, the tubular housing having an internal volume substantially equal to one said desired predetermined volumes of liquid to be dispensed;

(b) a shear valve directly connected to the proximal end of said aspiration probe, said shear valve having an aliquoting chamber with a volume substantially equal to another one of said desired predetermined volumes of liquid to be dispensed, said shear valve being actuatable to trap aspirated liquid within said aspiration probe and said aliquoting chamber;

(c) aspiration means for causing liquid in the container to enter the distal end of said aspiration probe and to completely fill the internal volume of said tubular housing of said aspiration probe and said aliquoting chamber of said shear valve, whereby the aspiration probe contains said desired predetermined volume of liquid;

(d) sensing means for sensing that the tubular housing is completely filled with aspirated liquid;

(e) sensing means operatively coupled and responsive to the means for actuating said shear valve to trap the aspirated liquid in the aspiration probe and in said aliquoting chamber of said shear valve; and (f) means for dispensing the trapped aspirated liquids in said probe and in said aliquoting chamber.

9. The apparatus as defined by claim 8 wherein said shear valve comprises first, second and third plates arranged in contiguous relationship, said second plate being disposed between said first and third plates and said aspiration probe being directly connected to said first plate, each of said plates having a pair of opposing planar faces and a first bore hole therebetween to enable liquid flow through said plate, said first, second and third plates being slidably movable relative to each other for movement between a first position in which their respective first bore holes are aligned so as to enable aspiration of a blood sample from said container through said valve, and a second position in which the respective bore holes in said plates are misaligned so as to prevent liquid flow through said valve and to trap aspirated liquid within said tubular housing of said aspiration probe and within the first bore hole of said second plate.

10. The apparatus as defined by claim 9 wherein each of said first, second and third plate further comprises second and third bore hole for enabling the dispensing of liquid trapped in the first bore hole of said second plate, and for enabling the rinsing of liquid trapped in the first bore hole of said third plate, said within said bore hole of said first plate, the respective second bore holes of said plates, and the respective third bore holes of said plates being aligned with each other when said first, second and third plates are in their respective second positions relative to each other.

* * * * *